United States Patent
Kung et al.

(10) Patent No.: US 7,480,045 B2
(45) Date of Patent: Jan. 20, 2009

(54) CONTROLLING PULSES IN OPTICAL MICROSCOPY

(75) Inventors: Andy Kung, Taipei (TW); Tse-Luen Wee, Taipei (TW); Shu-Wei Huang, Yunlin County (TW)

(73) Assignee: Academia Sinica, Nan-Kang Taipei (TW)

( * ) Notice: Subject to any disclaimer, the term of this patent is extended or adjusted under 35 U.S.C. 154(b) by 318 days.

(21) Appl. No.: 11/554,713

(22) Filed: Oct. 31, 2006

(65) Prior Publication Data

US 2008/0100834 A1 May 1, 2008

(51) Int. Cl.
G01N 21/63 (2006.01)
G01N 21/64 (2006.01)
G01N 21/65 (2006.01)

(52) U.S. Cl. .................. 356/311; 356/318; 356/417; 356/301; 250/458.1

(58) Field of Classification Search ................. 356/301, 356/311, 317, 318, 417
See application file for complete search history.

(56) References Cited

U.S. PATENT DOCUMENTS

| | | | |
|---|---|---|---|
| 5,034,613 A | 7/1991 | Denk et al. | |
| 5,275,168 A | 1/1994 | Reintjes et al. | |
| 6,108,081 A | 8/2000 | Holtom et al. | |
| 6,166,385 A | 12/2000 | Webb et al. | |
| 6,356,088 B1 | 3/2002 | Simon et al. | |
| 6,466,040 B1 | 10/2002 | Simon et al. | |
| 6,798,507 B2 | 9/2004 | Xie et al. | |
| 6,809,814 B2 | 10/2004 | Xie et al. | |

2004/0057047 A1 3/2004 Knebel

OTHER PUBLICATIONS

Hopt et al., Highly Nonlinear Photodamage in Two-Photon Fluorescence Microscopy, Biophysical Journal, vol. 80, Apr. 2001, pp. 2029-2036.*
Helmchen, F. & W. Denk, "Deep Tissue Two-Photon Microscopy" *Nature Methods*, vol. 2, No. 12, Dec. 2005 (pp. 932-940).
Wang et al., "In Vitro and In Vivo Two-Photon Luminescence Imaging of Single Gold Nanorods" *PNAS*, vol. 102, No. 44, Nov. 1, 2005 (pp. 15752-15756).
Becker et al., "FRET Measurements by TCSPC Laser Scanning Microscopy" European Conferences on Biomedical Optics, ECBO 2001, Munic, Jun. 2001.
Rehman, S. & P.B. Lukins, "Picosecond Time-Gated Microscopy of UV-damaged Plant Tissue" *Optics Express*, vol. 10, No. 8, Apr. 22, 2002, (pp. 370-375).
Booth, M. J. & S. W. Hell, "Continuous Wave Excitation Two-Photon Fluorescence Microscopy Exemplified with the 647-nm ArKr Laser Line" Journal of Microscopy, vol. 190, Pt. 3, Jun. 1998 (pp. 298-304).

* cited by examiner

*Primary Examiner*—F. L Evans
(74) *Attorney, Agent, or Firm*—Fish & Richardson P.C.

(57) ABSTRACT

A method for imaging a sample is described. The sample is characterized by a limit on incident optical energy absorbed over a given time period. The method includes providing at least one input optical wave that includes pulses that each have a full-width half-maximum time duration of more than 100 picoseconds and a pulse energy sufficiently large such that a sufficient number of consecutive pulses absorbed by the sample would exceed the limit. The method also includes directing the input optical wave to focus on a first portion of the sample; detecting energy from an output optical wave generated from a nonlinear optical interaction in the first portion of the sample with the input optical wave; and generating a representation of the first portion of the sample based on the detected energy from the output optical wave.

56 Claims, 7 Drawing Sheets

CONTROLLING PULSES IN OPTICAL MICROSCOPY

BACKGROUND

The invention relates to controlling pulses in optical microscopy.

Various techniques for optical microscopy can be used to construct an image of a portion of a tissue sample. Some techniques for optical microscopy use nonlinear optical interactions in the tissue being imaged to provide an optical signal that can be measured to construct the image of the tissue. Nonlinear optical techniques facilitate acquisition of images deep within a sample to form, for example, three-dimensional images of biomedical samples hidden underneath non-transparent tissues, or images of defects and impurity contents situated inside light absorbing materials.

Nonlinear optical microscopy techniques include, for example, multiphoton excitation techniques such as two-photon-excited fluorescence laser scanning microscopy (2PLSM), techniques based on three-wave mixing such as second-harmonic generation, and techniques based on four-wave mixing such as third-harmonic generation and coherent anti-Stokes Raman scattering (CARS). Multiphoton excitation of a sample by a laser can be combined with any of a variety of optical detection techniques including fluorescence emission, harmonic generation, Raman or Brillouin scattering, or with non-optical thermal or electronic detection techniques.

In linear optical microscopy, the photons of an optical wave incident on a tissue sample are either scattered by the tissue or excite target molecules (e.g., fluorescent dyes) to provide signal photons that are collected by an imaging system to generate a detected signal. The detected signal depends linearly on the incident optical wave intensity. In nonlinear optical microscopy, the detected signal depends nonlinearly on the incident optical wave intensity, or in some cases, depends on the intensities of multiple interacting optical waves. However, the efficiency of nonlinear interactions are typically weak and therefore call for optical waves with high peak intensities. Ultrafast modelocked lasers are used to provide pulses with high peak intensity and short time duration (full-width half-maximum (FWHM) time duration). Modelocking provides regularly spaced pulses having a well-defined shape (e.g., approximately Gaussian).

SUMMARY

In one aspect, in general, the invention features a method for imaging a sample. The sample is characterized by a limit on incident optical energy absorbed over a given time period. The method includes providing at least one input optical wave that includes pulses that each have a full-width half-maximum time duration of more than 100 picoseconds and a pulse energy sufficiently large such that a sufficient number of consecutive pulses absorbed by the sample would exceed the limit. The method also includes directing the input optical wave to focus on a first portion of the sample; detecting energy from an output optical wave generated from a nonlinear optical interaction in the first portion of the sample with the input optical wave; and generating a representation of the first portion of the sample based on the detected energy from the output optical wave.

Aspects of the invention can include one or more of the following features.

The input optical wave includes pulses that each have a full-width half-maximum time duration of more than 500 picoseconds.

The input optical wave includes pulses that each have a full-width half-maximum time duration of more than 1 nanosecond.

The input optical wave includes pulses that each have a full-width half-maximum time duration of more than 10 nanoseconds.

The input optical wave includes pulses that each have a full-width half-maximum time duration of more than 100 nanoseconds.

The method further includes temporarily preventing the input optical wave from reaching the sample.

Temporarily preventing the input optical wave from reaching the sample includes periodically preventing the input optical wave from reaching the sample.

Temporarily preventing the input optical wave from reaching the sample includes preventing the optical wave from reaching the sample before a number of consecutive pulses are absorbed by the sample would exceed the limit.

The nonlinear optical interaction comprises multi-photon absorption.

The nonlinear optical interaction comprises two-photon absorption.

The output optical wave comprises a fluorescence emission from the sample.

The fluorescence emission from the sample comprises emission from a fluorescent molecule in the sample.

The nonlinear optical interaction comprises wave mixing.

The nonlinear optical interaction comprises four-wave mixing.

The nonlinear optical interaction comprises coherent anti-Stokes Raman scattering.

Providing at least one input optical wave, directing the input optical wave, and detecting energy from the output optical wave comprise: providing at least two input optical waves that include pulses that each have a full-width half-maximum time duration of more than 100 picoseconds; directing the input optical waves to focus on a first portion of the sample; and detecting energy from an output optical wave generated from a wave mixing interaction in the first portion of the sample with each of the input optical waves.

Providing at least two input optical waves comprises providing signal and idler optical waves generated from parametric downconversion of a pump optical wave that includes pulses that each have a full-width half-maximum time duration of more than 100 picoseconds.

The method further includes moving the input optical wave relative to the sample to focus on a second portion of the sample; detecting energy from an output optical wave generated from a nonlinear optical interaction in the second portion of the sample with the input optical wave; generating a representation of the second portion of the sample based on the detected energy from the output optical wave; and generating an image of the sample that includes the representation of the first portion of the sample and the representation of the second portion of the sample.

In another aspect, in general, the invention features a method for imaging a sample including providing at least one input optical wave that includes pulses that are approximately uniformly spaced by a time delay; directing the input optical wave to focus on a first portion of the sample; detecting energy from an output optical wave generated from a nonlinear optical interaction in the first portion of the sample with the optical wave during a first time period that is about equal to or longer than the time delay; temporarily preventing the input optical wave from reaching the sample during a second time period that is long enough for most of an amount of heat built up in the sample by the input optical wave during the first time period to be dissipated; and generating a representation of the first portion of the sample based on the detected energy from the output optical wave.

Aspects of the invention can include one or more of the following features.

The first time period is short enough to prevent damage to the sample caused by the amount of heat built up in the sample by the input optical wave during the first time period.

The first time period is shorter than 500 milliseconds.

The first time period is shorter than 100 milliseconds.

The first time period is shorter than 10 milliseconds.

The first time period is shorter than 1 millisecond.

The first time period is longer than twice the time delay.

Detecting the energy from the output optical wave and temporarily preventing the input optical wave from reaching the sample are repeated approximately periodically during multiple respective first and second time periods with the input optical wave directed to focus on different portions of the sample.

Detecting energy from the output optical wave during the first time period comprises processing detected energy during respective time windows that are shorter than the time delay and rejecting detected energy from the sample outside of the time windows.

The time windows are synchronized to respective pulses in the input optical wave.

Rejecting detected energy from the sample outside of the time windows comprises preventing detection of energy from the sample outside of the time windows.

Rejecting detected energy from the sample outside of the time windows comprises preventing processing of portions of a stored signal that correspond to energy detected outside of the time windows.

The method further includes moving the input optical wave relative to the sample to focus on a second portion of the sample.

The input optical wave is moved relative to the sample during the second time period.

Moving the input optical wave relative to the sample comprises moving the input optical wave without moving the sample.

Moving the input optical wave relative to the sample comprises moving the sample without moving the input optical wave.

The method further includes detecting energy from an output optical wave generated from a nonlinear optical interaction in the second portion of the sample with the input optical wave; generating a representation of the second portion of the sample based on the detected energy from the output optical wave; and generating an image of the sample that includes the representation of the first portion of the sample and the representation of the second portion of the sample.

The input optical wave includes pulses that each have a full-width half-maximum time duration of more than 100 picoseconds.

The input optical wave includes pulses that each have a full-width half-maximum time duration of more than 1 nanosecond.

The time delay is between about 1 microsecond and about 1 millisecond.

The time delay is between about 10 microseconds and about 100 microseconds.

The nonlinear optical interaction comprises multi-photon absorption.

The nonlinear optical interaction comprises two-photon absorption.

The output optical wave comprises a fluorescence emission from the sample.

The fluorescence emission from the sample comprises emission from a fluorescent molecule in the sample.

The nonlinear optical interaction comprises wave mixing.

The nonlinear optical interaction comprises four-wave mixing.

The nonlinear optical interaction comprises coherent anti-Stokes Raman scattering.

Providing at least one input optical wave, directing the input optical wave, and detecting energy from the output optical wave comprise: providing at least two input optical waves that include pulses; directing the input optical waves to focus on a first portion of the sample; and detecting energy from an output optical wave generated from a wave mixing interaction in the first portion of the sample with each of the input optical waves.

Providing at least two input optical waves comprises providing signal and idler optical waves generated from parametric downconversion of a pump optical wave that includes pulses.

In another aspect, in general, the invention features a system for imaging a sample characterized by a limit on incident optical energy absorbed over a given time period. The system includes a source of at least one input optical wave that includes pulses that each have a full-width half-maximum time duration of more than 100 picoseconds and a pulse energy sufficiently large such that a sufficient number of consecutive pulses absorbed by the sample would exceed the limit; a microscope configured to direct the input optical wave to focus on a first portion of the sample; and a detection sub-system configured to detect energy from an output optical wave generated from a nonlinear optical interaction in the first portion of the sample with the input optical wave, and generate a representation of the first portion of the sample based on the detected energy from the output optical wave.

Aspects of the invention can include one or more of the following features.

The source is configured to temporarily prevent the input optical wave from reaching the sample.

Temporarily preventing the input optical wave from reaching the sample includes periodically preventing the input optical wave from reaching the sample.

Temporarily preventing the input optical wave from reaching the sample includes preventing the optical wave from reaching the sample before a number of consecutive pulses are absorbed by the sample would exceed the limit.

The system further includes excitation optics between the source and the microscope configured to periodically prevent the input optical wave from reaching the sample.

The detection sub-system is configured to process energy that has been detected within time windows corresponding to the pulses.

The detection sub-system is configured to prevent detection of energy outside of the time windows.

The detection sub-system is configured to remove portions of a signal corresponding to energy detected outside of the time windows.

Aspects of the invention can have one or more of the following advantages.

Techniques described herein for managing the timing of an excitation optical wave and the associated signal collection may reduce potential for damage due to heat, and increase quality of the signal (e.g., signal-to-noise ratio). Since the pulses are relatively long (e.g., >100 ps) and the pulse repetition rate is relatively low (e.g., <1 MHz), time gated signal processing can be performed at speeds that the detection electronics can handle. Without a need for an ultrafast laser, the system for nonlinear optical microscopy applications will be compact, reliable, and simple to operate. The fixed and the tunable near infrared wavelengths of some of the laser sources are able to penetrate biological tissues or materials such as silicon to reveal images embedded deep inside these samples. In wavelength scanning applications as in mode-selective molecular or biological imaging, the wavelength of lasers with relatively longer pulses can be tuned or scanned relatively easily and rapidly compared to short pulse tunable lasers.

Unless otherwise defined, all technical and scientific terms used herein have the same meaning as commonly understood by one of ordinary skill in the art to which this invention belongs. In case of conflict with publications, patent applications, patents, and other references mentioned incorporated herein by reference, the present specification, including definitions, will control.

Other features and advantages of the invention will become apparent from the following description, and from the claims.

DESCRIPTION

Figure 1:
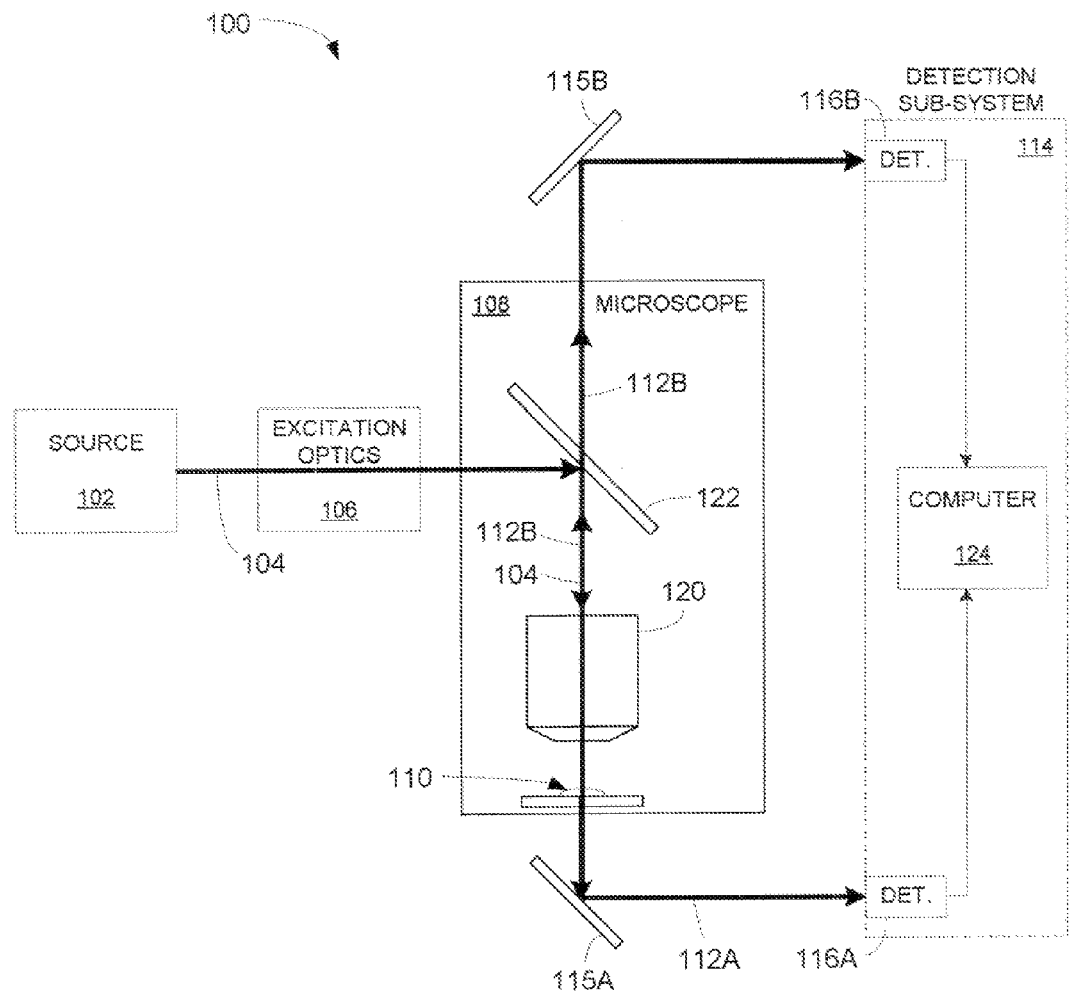
FIG. 1 is a diagram of a nonlinear optical microscopy system.

Some techniques for obtaining high-quality images of a sample using nonlinear optical microscopy include the use of an input optical wave comprising a series of optical pulses each having a high peak electric field intensity. There are factors that limit the highest intensity that can be tolerated in a sample (e.g., a biological tissue sample). Two limiting factors are optical damage and thermal damage of the sample. Optical damage includes damage of the sample caused by a large electric field intensity, which places a limit on the peak power density (W/cm$^2$) of pulses. Thermal damage includes damage of the sample caused by heating of the sample to above a tolerable temperature due to absorption of the optical energy over time, which places a limit on the average power density of a stream of pulses, or on the energy density (J/cm$^2$) or "fluence" of each pulse and the pulse repetition rate.

The limits on characteristics of an optical wave associated with limiting optical and thermal damage depend on the sample. For many biological samples (e.g., cells or viruses), a typical optical damage limit on peak power density is approximately 10-100 GW/cm$^2$, and a typical thermal damage limit on average power density is approximately 10 MW/cm$^2$. In many cases, thermal damage is more limiting than optical damage. Typically, short pulse lasers with pulse durations in the picosecond and sub-picosecond regime are used to provide pulses with relatively high peak power density for high-quality imaging, but relatively low average power density (due to low pulse energy) to reduce the potential for thermal damage to the sample. Short pulse lasers can be, in general, relatively complex, difficult to operate, and expensive compared to lasers with longer pulse durations.

Various classes of lasers can become less complex, easier to operate, and less expensive as the pulse durations become longer (e.g., >100 ps, >500 ps, >1 ns, >10 ns, or >100 ns). Another benefit of longer pulse durations is the associated reduction in minimum linewidth of the spectrum of the optical wave. Some spectroscopic techniques, such as CARS, scan the peak wavelength of a source's spectral line to probe the spectral properties of a sample. Not only is such wavelength scanning more complex in a short pulse source, but the spectral resolution attainable is lower due to the larger minimum linewidth. When optical wave from a short pulse source is coupled into an optical fiber (e.g., to improve delivery and alignment of the optical wave into a microscope), group velocity dispersion may result in chirping and temporal distortion of the pulses. Nonlinear processes may also occur in the fiber, altering the spectral characteristics of the optical wave.

Coherent optical sources that provide long pulse duration optical waves (e.g., >100 ps) have been deemed by some as not suitable for nonlinear optical microscopy due to potential for damage to a sample and the lower image quality resulting from a reduced peak power density. However, by controlling the timing characteristics and delivery of an optical wave to a sample as described herein, it is possible to achieve high quality (e.g., low noise) images in nonlinear optical microscopy of the sample using longer pulse sources while satisfying damage constraints. Compact solid state pulsed lasers such as diode-laser-pumped Q-switched Nd ion doped YAG, YVO4, and YLF lasers, and Yb:doped fiber lasers and amplifiers can provide intense pulses with a time duration from a few nanoseconds to tens of nanoseconds and with excellent beam quality. The pulse repetition rates for these sources can be on the order of 1 kHz to 1 MHz. Such sources are compact, simple, and relatively inexpensive compared to short pulse lasers. The peak power of these lasers can be in the 1-10 kW range, about 10 times less than typical short pulse lasers with pulse durations in the picosecond and sub-picosecond regime. The typical pulse energy of these diode-laser pumped solid state lasers is correspondingly higher than that of short pulse lasers by about 100 to 500 times.

By managing the timing of an excitation optical wave and the associated signal collection, it is possible to avoid thermal damage while producing high-resolution microscopic images of good quality. Thermal damage can result from a rapid increase in temperature following accumulation of absorbed energy. If the excitation optical wave is temporarily prevented from reaching (or being absorbed in) the sample before the temperature reaches a destructive value, then accumulated heat has time to dissipate away from the sample so that damage does not occur.

1 System Overview

Referring to FIG. 1, in a nonlinear optical microscopy system 100, a source 102 provides an input optical wave 104 that includes pulses that are approximately uniformly spaced by an inter-pulse time delay τ. The source 102 is a long-pulse source such that each pulse has a full-width half-maximum time duration of more than about 100 picoseconds. Excitation optics 106 direct the input optical wave 104 to a microscope 108 that focuses the wave 104 onto a portion of a sample 110 to be imaged. The input optical wave 104 serves as input for a nonlinear optical interaction in that portion of the sample 110. The excitation optics 106 can direct the optical wave 104 to the microscope 108 over free space or guided within an optical fiber, for example. For free space delivery, the excitation optics 106 can include a lens followed by a pinhole followed by another lens to clean up the transverse mode of the beam from the source 102 and to adapt the diameter of the beam to the diameter of an entrance window of a microscope objective lens 120 to provide adequate spatial resolution. The excitation optics 106 can also include attenuation elements such as neutral density filters or a polarization rotator and polarizer pair for controlling the intensity of the input optical wave 104.

The nonlinear optical interaction in the sample 110 can generate an output optical wave 112A that travels in a forward direction relative to the input optical wave 104 to be detected in a "trans-collection" mode, and/or an output optical wave 112B that travels in a backward direction relative to the input optical wave 104 to be detected in an "epi-collection" mode. The output optical waves 112A and 112B are directed by mirrors 115A and 115B, respectively, to a detection sub-system 114 to generate an image of the sample 110. The output optical waves 112A and 112B can represent a fluorescence signal, or an optical harmonic signal, or a Raman shifted or anti-Stokes shifted signal of the input optical wave 104, for example. Due to the nature of nonlinear optical processes, generation of these signals is typically substantially localized to the focus of the input optical wave 104, where the intensity is greatest. This transverse and longitudinal localization of the interaction at the beam focus enables three-dimensional discrimination of the imaged location.

The output optical wave 112A is detected in a trans-collection mode at a first detector 116A, and the output optical wave 112B is detected in an epi-collection mode at a second detector 116B. In trans-collection mode, the forward propagating output optical wave 112A can be collected after propagating through the sample 110 to the detector 116A. In epi-collection mode, the backward propagating output optical wave 112B can be propagate back through the microscope objective lens 120 and through a dichroic beam splitter (DBS) 122 that reflects most of the input optical wave 104 and transmits most of the output optical wave 112B. In either mode, the output optical waves 112A and 112B can be filtered by one or more narrowband filters to discriminate from the intense input optical wave 104 and focused by one or more lenses before being detected. The detection sub-system 114 can include any of a variety of detector types including a photodiode, a charge-coupled device, or photon counters such as a photomultiplier or an avalanche photodiode.

The nonlinear optical microscopy system 100 can include components such as galvanometric mirrors to move the input optical wave 104 (e.g., within the excitation optics 106), a motorized/piezoelectric stage to move the sample 110, or both, to scan over different portions of the sample 110 and build up an image (over x and y dimensions). Three-dimensional images can be obtained by further moving the microscope objective focus (e.g., by a piezoelectric transducer) to take image "slices" in different planes (along a z dimension). The image can be represented, for example, as a collection of image elements such as "pixels" of a two-dimensional image, or a "voxels" of a three-dimensional image that represent a property of the sample 110 based on the energy detected from the output optical waves 112A and/or 112B. For example, a property of the sample 110 may be related to an intensity of fluorescence emission resulting from 2PLSM, and the energy in the output optical waves 112A and/or 112B collected in response to one of the pulses in the input optical wave 104 can quantify that property at a sample location. Each image element can be represented as scalar data or vector data (e.g., representing spectral properties of a portion of the sample 110) stored on a memory storage medium. For example, the detection sub-system 114 can include a computer system 124 having a memory storage medium such as a hard drive.

Some implementations of the system 100 use more than one input optical wave from the source 102. For example, an implementation of the system 100 for CARS microscopy uses two input optical waves having different frequencies. The difference of the frequencies corresponds to the Raman transition frequency of the sample 110. The two optical waves mix in a nonlinear interaction in the sample 110 to generate a CARS output optical wave that is detected.

A tunable optical parametric oscillator (OPO) pumped by a pulsed laser can be used as the source 102 of two substantially collinear output optical waves: a signal wave and an idler wave. If the OPO is pumped with a pulsed wave, the signal and idler waves will include pulses that are automatically overlapped in time. The sum of the frequencies of the signal wave and the idler wave equals the frequency of the pump wave. Techniques for tuning the OPO include, for example, tuning the pump frequency and/or tuning the phase matching condition among the pump, signal, and idler. The difference of the signal and idler frequencies (and wavelengths) then can be scanned appropriately to excite the Raman transitions of the chemical bonds of the sample species that is to be imaged. An example of a tunable OPO that can be used as a source is described in U.S. application Ser. No. 11/318,234, filed on Dec. 23, 2005, incorporated herein by reference.

An advantage of using an OPO is that the signal, idler and output CARS signal wavelengths fall in the transmission window of most tissues so that absorption and scattering loss are kept to a minimum, allowing for penetration of the light deep inside the tissue sample to make images that cannot be observed by visible microscopy or short pulse scanning microscopy at 790 nm, a commonly used wavelength in short pulse microscopes. The output spectral bandwidth of about 1 cm$^{-1}$ of nanosecond OPOs can be much narrower than that of most femtosecond or picosecond OPOs, thus the system 100 will be able to obtain a CARS signal spectrum with better spectral resolution and better species selectivity.

Other types of sources can be used for nonlinear interactions with multiple input optical waves. For example, the source 102 can include an OPO pumped by a second harmonic of a laser and various combinations of the fundamental, SHG-pump, signal, and idler waves can be used as input optical waves.

2 System Operation

Figure 2A:
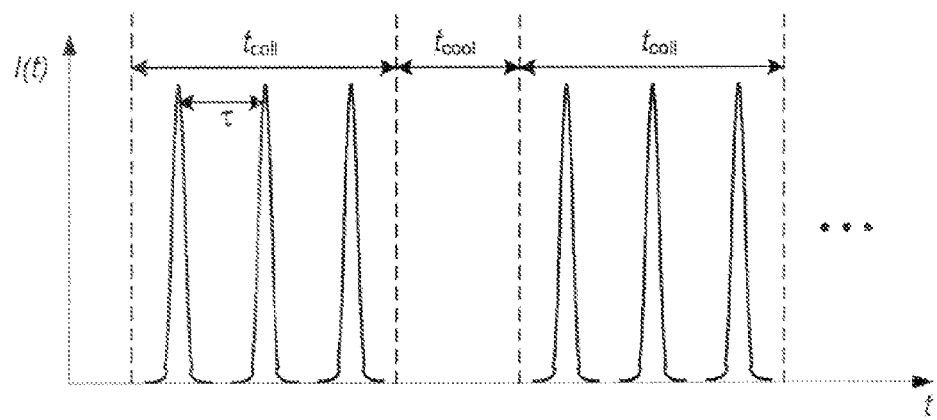
FIG. 2A is a plot of intensity of an input optical wave.
Figure 2B:
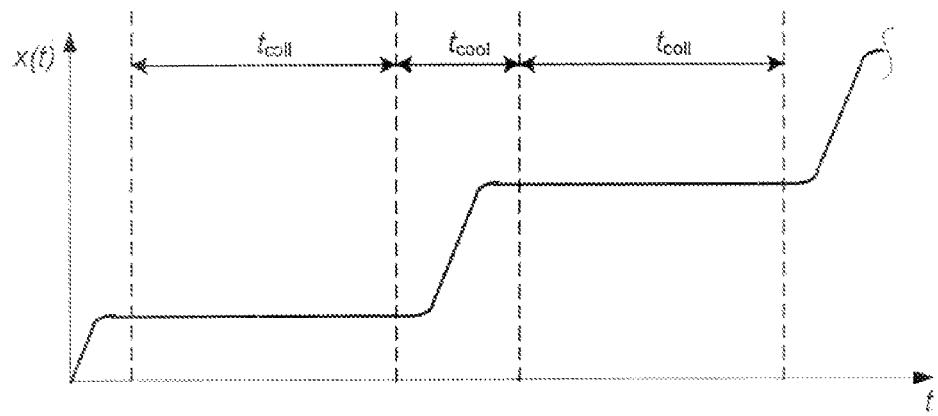
FIG. 2B is a plot of the position of the input optical wave of FIG. 2A relative to a sample.
Figure 2C:
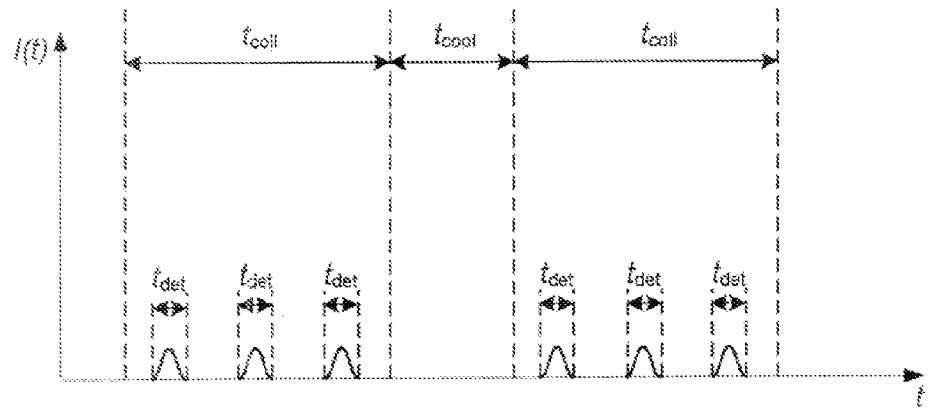
FIG. 2C is a plot of intensity of an output optical wave.

Referring to FIGS. 2A-2C, the system 100 is configured to collect an output optical wave 112A and/or 112B generated from the nonlinear optical interaction in the sample 110 during a collection time period $t_{coll}$, and to temporarily prevent the optical wave 104 from reaching the sample 110 during a cooling time period $t_{cool}$. The cooling time period is long enough for most of an amount of heat built up in the sample 110 by the optical wave 104 during the collection time period to be dissipated. For example, the source 102 can include a switching mechanism that periodically stops pumping the source 102 (e.g., by turning off a power supply) to quench a lasing process that generates the optical wave 104. Alternatively, instead of quenching or otherwise shutting off the source 102, the system 100 can block or divert the optical wave 104, for example, using an optical device (e.g., an acousto-optic modulator) or a mechanical device (e.g., a electromechanical shutter or a piezoelectrically controlled mirror) within the excitation optics 106.

For typical diode-laser-pumped solid state lasers, to provide an average power density below the thermal damage limit, the collection time period $t_{coll}$ can be in the range of about 1 msec to 500 msec for a given portion of the sample that is being imaged with a beam spot size at the focal plane of the optical wave 104 of about 0.25 µm$^2$ to 1 µm$^2$. Since no signal is detected during the cooling time period $t_{cool}$, this cooling time can be used to move the optical wave 104 relative to the sample 110 to focus on a different portion of the sample to be imaged (or "imaging spot"). Thus, the speed of scanning across imaging spots of the sample 110 does not need to be faster than the distance between neighboring spot locations divided by $t_{cool}$. The collection time period $t_{coll}$ is large enough to ensure sufficient signal is collected. In some implementations $t_{coll}$ is large compared to the inter-pulse time delay τ to encompass multiple pulses (i.e., $t_{coll}$>2τ), and is typically large enough to encompass tens or hundreds of pulses or more to excite the sample 110 during a collection time period at an imaging spot. For a collection time period of 500 ms, an optical wave 104 with a pulse repetition rate of 100 kHz would have 50,000 consecutive pulses absorbed by the sample 110 at each imaging spot. Alternatively, in some implementations, a single pulse could be sufficient to provide adequate signal.

FIG. 2A shows a plot of intensity I(t) of the input optical wave 104 at the sample 110 over a time span of a periodic waveform that shows two collection time periods separated by one cooling time period. In this example, to facilitate visualization, only three pulses occur within the collection time period. FIG. 2B shows a plot of a position x(t) of the optical wave 104 relative to the sample 110 in a linear scan across the sample. In this example, the cooling and scanning are synchronized such that the optical wave 104 is substantially stationary during each collection time period, and moves during each cooling time period. In other examples, the optical wave 104 may be stationary over multiple collection and cooling time periods.

To provide high quality images, sufficient signal energy (e.g., photon counts) from the output optical waves 112A and/or 112B should be collected during the collection time period to provide a high signal-to-noise ratio (SNR). The SNR can be increased by using time gated signal processing to process signal energy from the output optical waves 112A and/or 112B within limited detection time windows $t_{det}$ corresponding to each pulse. A controller (e.g., a computer) can use an electronic trigger pulse (e.g., from a driver that controls the pulsing of the source 102) to time the gating of the detection sub-system 114 to process energy that has been detected within the window $t_{det}$.

FIG. 2C shows a plot of intensity I(t) of the output optical waves 112A and/or 112B generated from the nonlinear optical interaction in the sample 110. The shape of the "signal pulses" in the wave (along with other characteristics such as spectrum, spatial mode, and propagation direction) depends on the specific interaction being utilized. The detection sub-system 114 is gated to process light detected within the detection time window $t_{det}$, but not to process light that is detected or would have been detected outside of this window. In this way, the detection sub-system 114 is likely to receive signal information based on the energy in the signal pulses that arrive at the detection sub-system 114 at a predictable time based on the regular excitation pulses, but to reject the noise that occurs outside of the window. Thus, potential noise from optical, electronic, and/or mechanical sources, for example, instead of from the nonlinear optical interaction is rejected. This increases the SNR and the resulting quality of the image.

Any of a variety of techniques can be used to perform the time gated signal processing. Gating can occur on-line, for example, by using electronic trigger pulses to gate a power supply within the detection sub-system 114 or to gate electronic amplifiers or photon counters within the detection sub-system 114. Alternatively, the gating can occur off-line by storing a detected signal into a computer and digitally processing the signal according to timing information. Thus, in an on-online approach, the detection sub-system 114 is configured to prevent detection of energy outside of the detection time windows, and in an off-line approach, the detection sub-system 114 is configured to remove portions of a signal corresponding to energy detected outside of the detection time windows.

Various techniques can be used in combination with the time gated signal processing. A technique that uses a lock-in amplifier or a boxcar amplifier for phase-sensitive signal detection is described in U.S. Pat. No. 6,356,088, incorporated herein by reference.

3 Working Example

The following is a working example of two-photon-excited fluorescence laser scanning microscopy (2PLSM) using an implementation of the nonlinear optical microscopy system 100.

Figure 3:
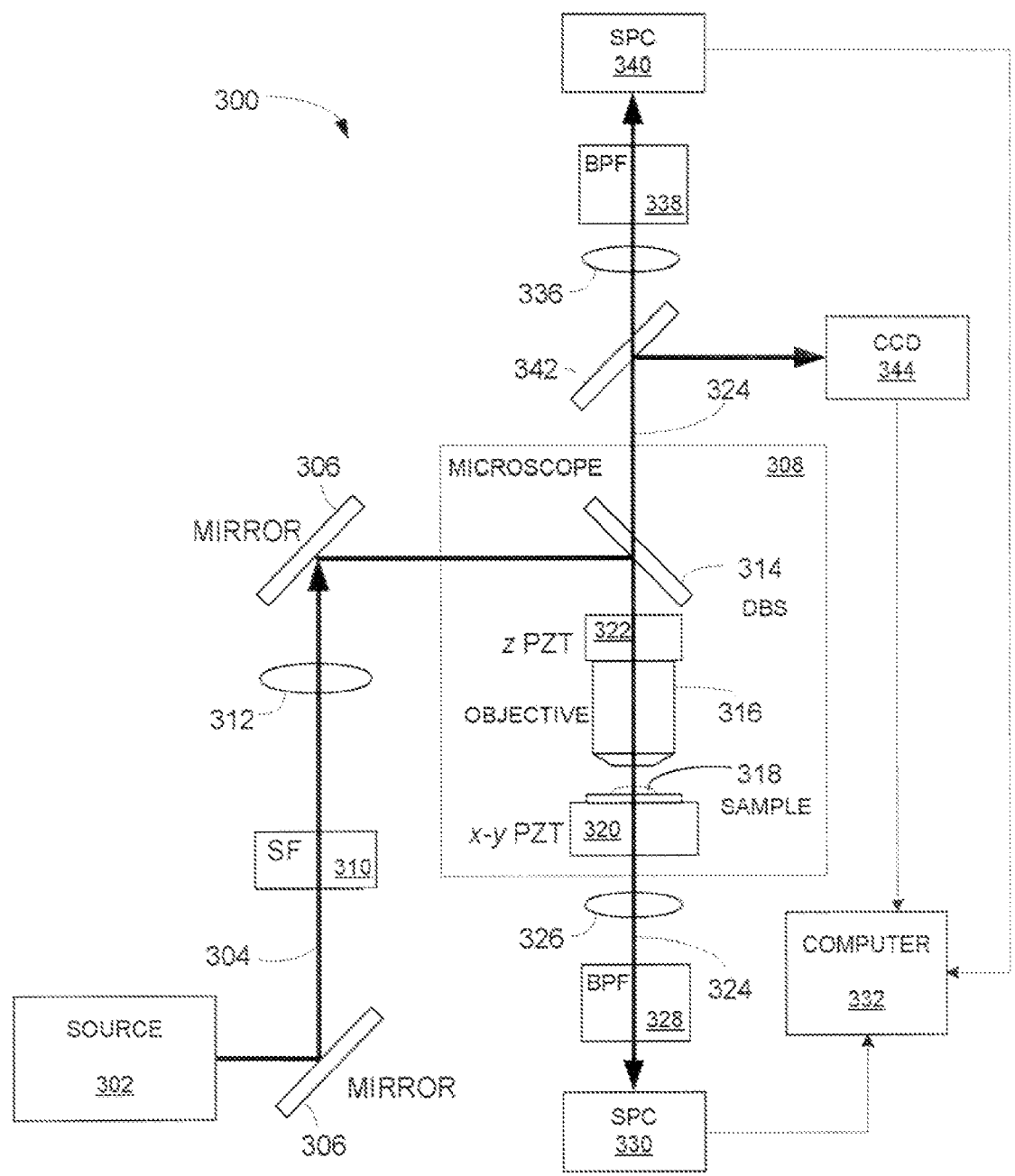
FIG. 3 is a diagraph of a system for two-photon-excited fluorescence laser scanning microscopy (2PLSM).

Referring to FIG. 3, a system 300 was used for 2PLSM to obtain fluorescence images of different sample species. After repeated scans, no damage to the samples were observed. The spatial resolution of the images obtained was less than 0.5 µm. A Q-switched Nd:YAG laser was used as a source 302 of an input optical wave 304 with a 1064 nm wavelength, a beam diameter of about 9 mm, a 10 kHz pulse repetition rate, and a 19 ns FWHM pulse width. Mirrors 306 directed the optical wave 304 into a microscope 308. A spatial filter 310 cleaned the spatial mode of the optical wave 304 and a lens 312 modematched the spatial mode into the microscope 308. The microscope 308 included a dichroic beam splitter (DBS) 314 to direct the optical wave 304 into a 40× objective lens 316 with a 0.8 numerical aperture (NA) in air. Each sample 318 was deposited on a glass slide placed on an x-y translation stage 320 equipped with a piezoelectric nanopositioner with a full scan range of 100 µm in each of the x and y directions. Fine adjustment in the z direction was performed with a one-dimensional piezoelectric transducer 322 attached to the objective lens 316.

A fluorescence optical wave 324 was collected by a lens 326 with a 0.68 NA, passed through a set 328 of narrowband bandpass filters, and detected by an avalanche photodiode single-photon counting module 330 in trans-collection mode. The photon counts were processed by a computer 332 to generate digital image to be stored and displayed. The fluorescence optical wave 324 was also collected back through the microscope 308 by a lens 336, passed through a set 338 of narrowband bandpass filters, and detected by an avalanche photodiode single-photon counting module 340 in epi-collection mode. A CCD detector 344 also collected a non-fluorescence image of the sample 318 from excitation light that leaked through the DBS 314 was reflected by a DBS 342.

Gated signal detection synchronized to the pulses of the input optical wave 304 was used to reduce any background signal to below the electronic noise limit of a few counts per second. The average power in the input optical wave 304 was typically around 16.5 mW, corresponding to a peak power of 90 W, a peak intensity of about 5.5 GW/cm², and a single pulse fluence of about 105 J/cm². A computer controlled the gating of the pulsed laser source 302 to start and stop the pulsed output from the laser so that the pulses were applied while the flurescence optical wave 324 was being collected and stopped while the sample 318 was being scanned.

The collection time period $t_{coll}$ was selected to limit the total fluence absorbed during $t_{coll}$ to below the damage threshold of the sample 318. This collection time period was experimentally determined for each sample species and was between about 50-100 ms. With these settings, the photon count per collection time period ranged from a few tens to several hundreds with a background count of less then five in each case. Under these conditions, the time it took to scan an image of 30 μm×30 μm was about 10-30 minutes. For other samples and/or excitation wavelengths, the thermal damage limits may allow scan times to be decreased by increasing the pulse repetition rate and reducing $t_{coll}$.

3.1 Sample 1: Photoresist Film

Figure 4B:
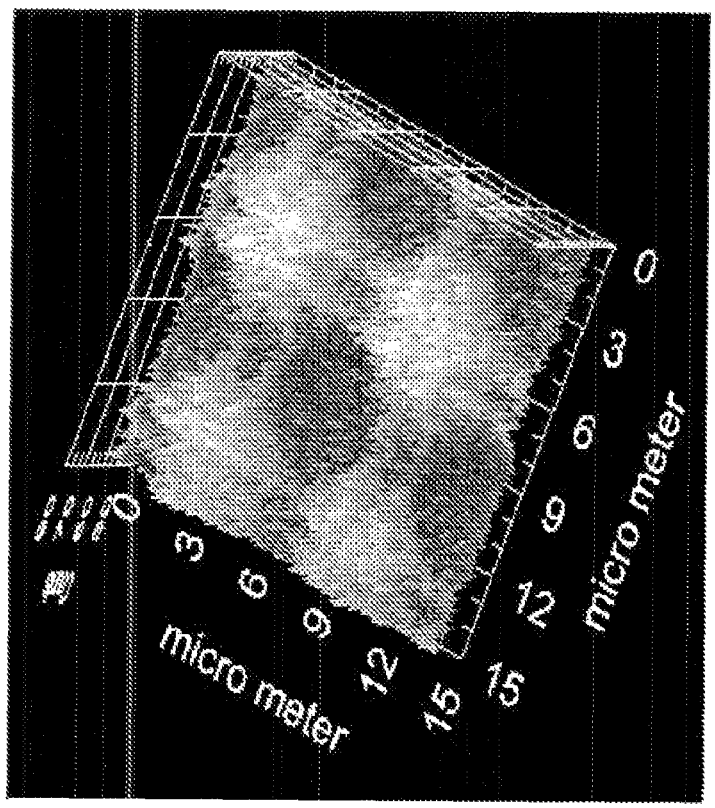
FIG. 4B is a 2PLSM image of a photoresist film sample.
Figure 4A:
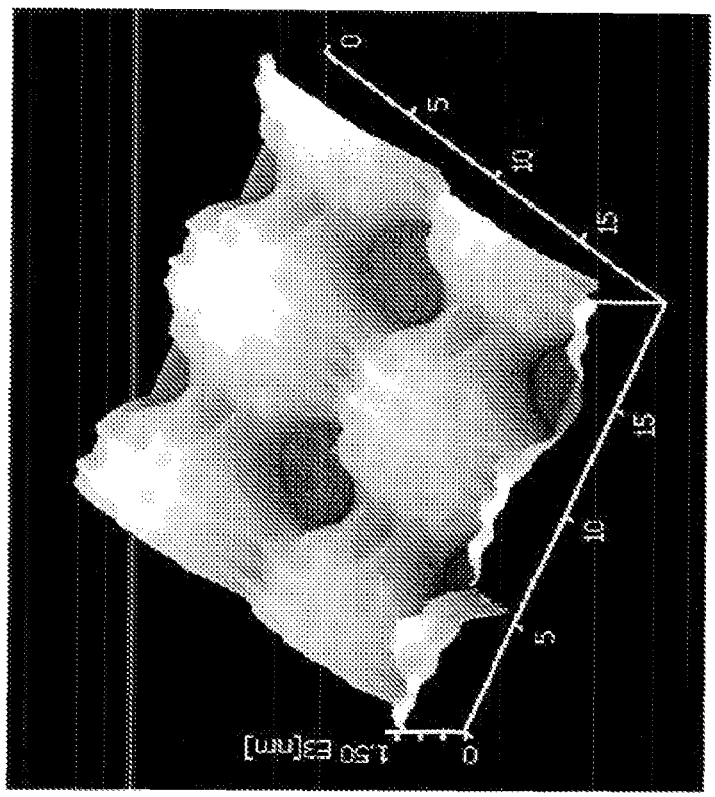
FIG. 4A is an AFM image of the photoresist film sample.

One sample imaged was an approximately 1 μm thick film of photoresist deposited on a glass slide and patterned into a two-dimensional (tetragonal) array of round holes (with diameter of ~3.2 μm and a depth of ~1.2 μm) using photolithography. FIG. 4B shows a 2PLSM image of the photoresist film sample. The photoresist polymer of which the film was composed yields a reasonable fluorescence signal at around 650 nm from two-photon excitation of ~10 mW of 1064 nm radiation, even though its fluorescence quantum yield is small compared to typical fluorescent dyes. The image shows clearly the openings etched into the photoresist by the photolithographic process, including a grid of fine lines that possibly resulted from optical interference due to the photolithographic process used to make the pattern. The spacing between the lines of the grid is about 1 μm. These features also appear in an atomic force microscope (AFM) image (with resolution<10 nm) of the same photoresist film shown in FIG. 4A.

3.2 Sample 2: Fluorospheres A

Figures 5A, 5B:
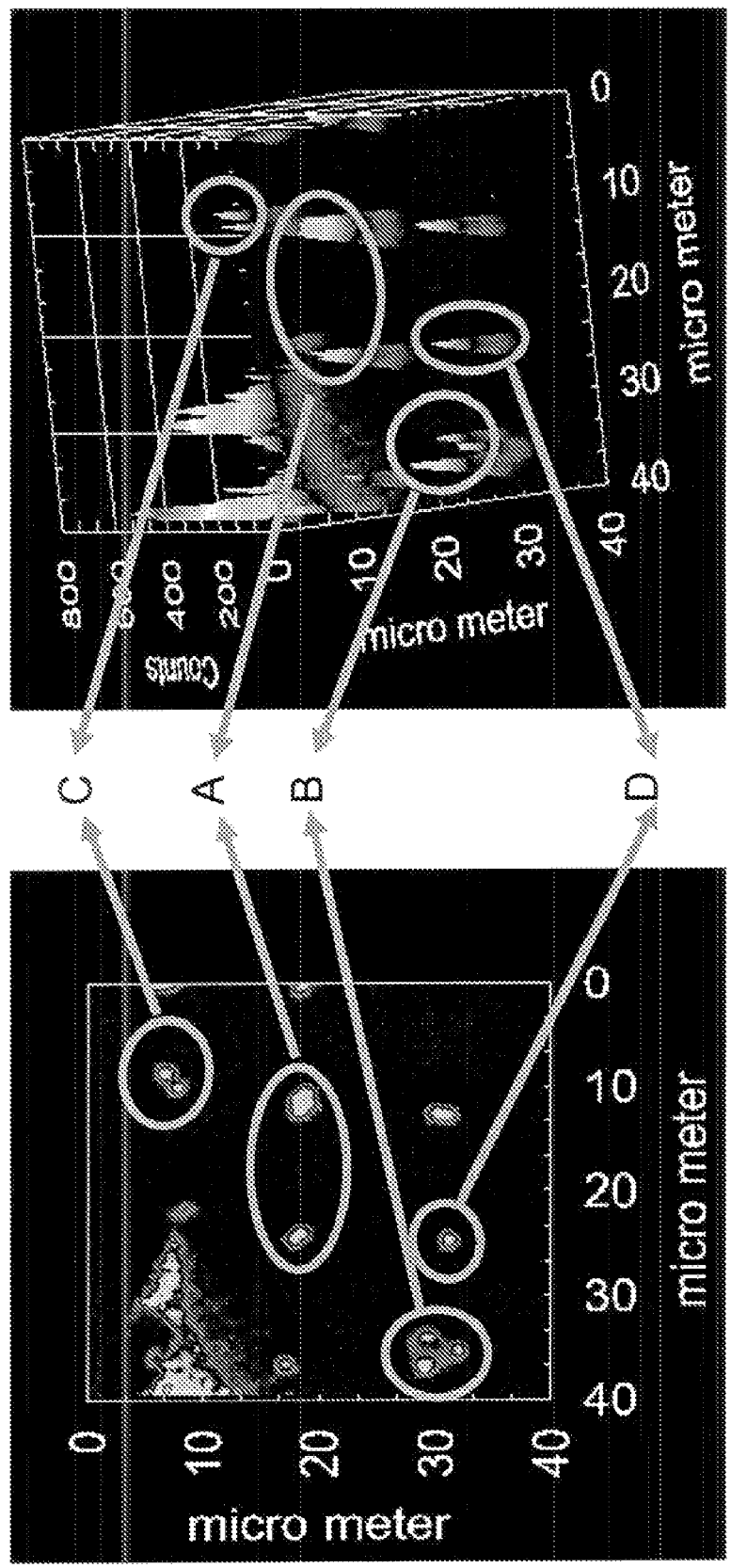
FIGS. 5A and 6A are two-dimensional 2PLSM images of fluorosphere samples.
FIGS. 5B and 6B are three-dimensional 2PLSM images of fluorosphere samples.

Another sample imaged was an emulsion of ~1.0 μm diameter fluorescent polystyrene microspheres (also called "molecular probes" or "fluorospheres") deposited into the patterned ~6.0 μm diameter holes of a photoresist film similar to that of Sample 1. FIG. 5A shows a two-dimensional 2PLSM image of the fluorosphere sample, and FIG. 5B shows a three-dimensional 2PLSM image of the fluorosphere sample. Various structural features of the deposition of the fluorospheres can be discerned from both images, including: (A) clusters of multiple fluorospheres in respective holes, (B) three distinguishable fluorospheres deposited into a hole, (C) two distinguishable fluorospheres deposited into a hole, and (D) a single fluorosphere deposited into a hole. In this example, the number of fluorospheres can be discerned by the size of the detected fluorescent portions of the image.

3.3 Sample 3: Fluoroshperes B

Figure 6B:
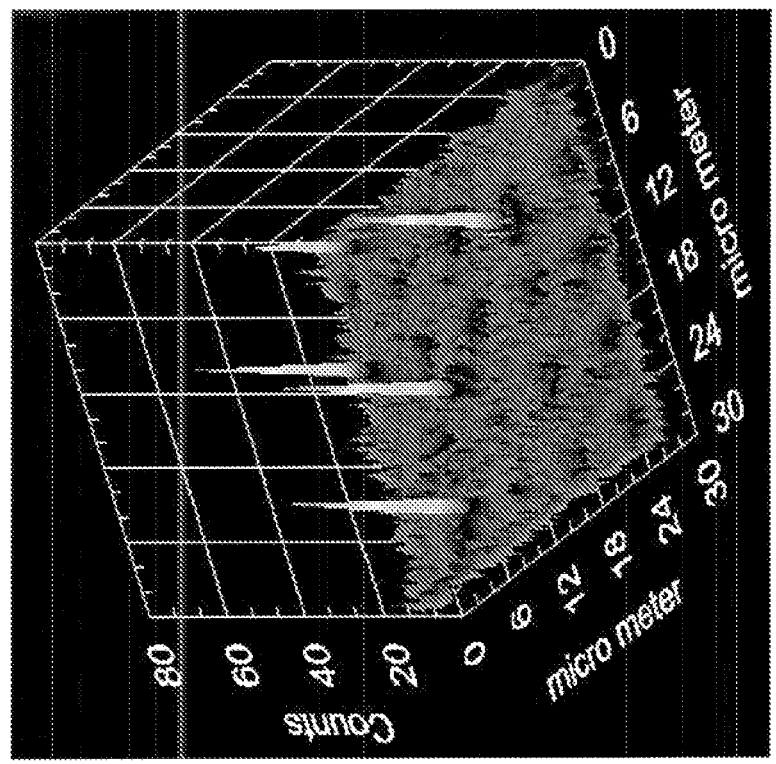
Figure 6A:
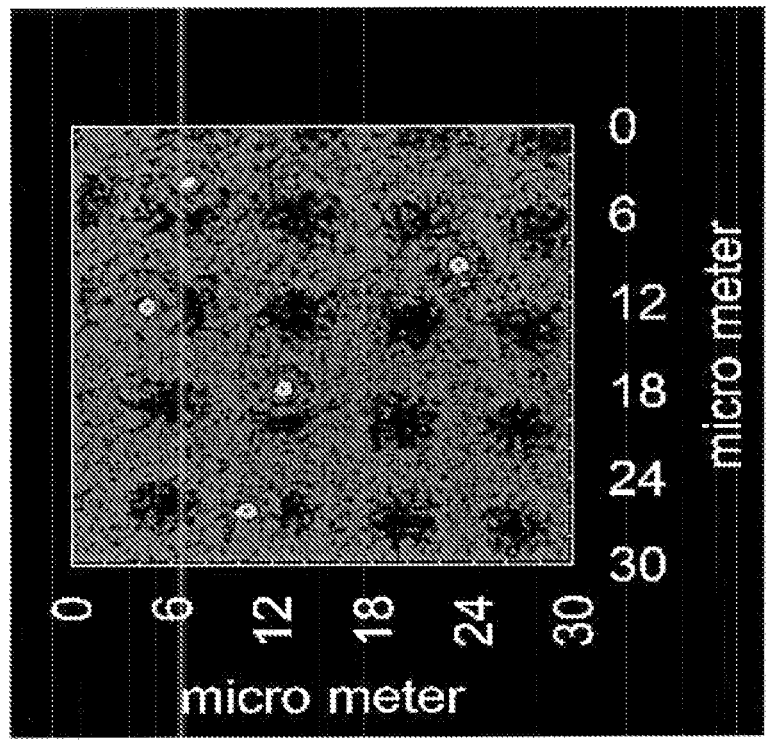

Another sample imaged was a dilute emulsion of ~0.5 μm diameter fluorescent polystyrene microspheres (also called "molecular probes" or "fluorospheres") deposited into the patterned ~2.9 μm diameter holes of a photoresist film. FIG. 6A, shows a two-dimensional 2PLSM image of the fluorosphere sample, and FIG. 6B shows a three-dimensional 2PLSM image of the fluorosphere sample. These images provide an estimate of the spatial resolution achieved in the 2PLSM imaging process using the system 300. From the slope of the three-dimensional image of a single bead, the spatial resolution achieved was <0.5 μm, close to the theoretical limit of ~0.35 μm due to diffraction of the 1064 nm laser wavelength within the system 300 in a two-photon process.

3.4 Sample 4: Onion

Figure 7B:
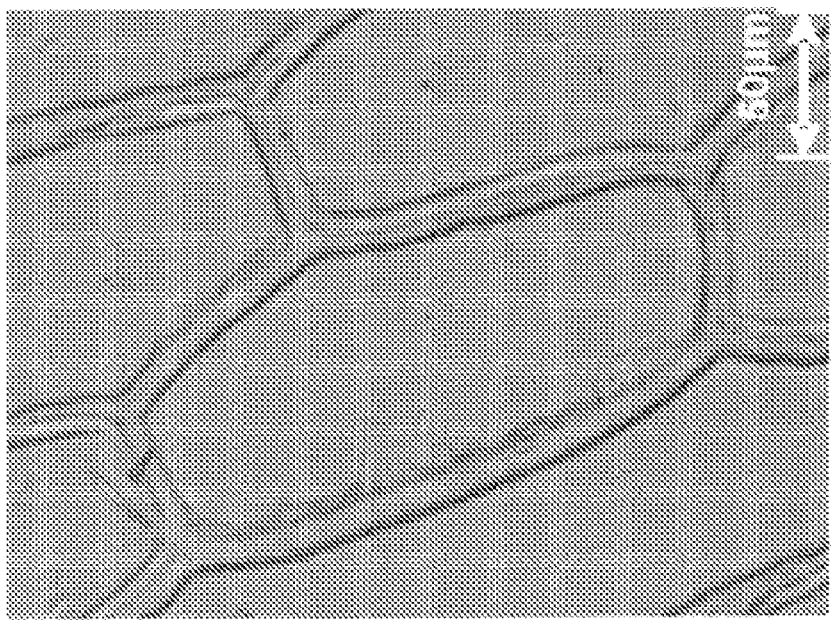
FIG. 7B is a white-light confocal microscopy image of the onion sample.
Figure 7A:
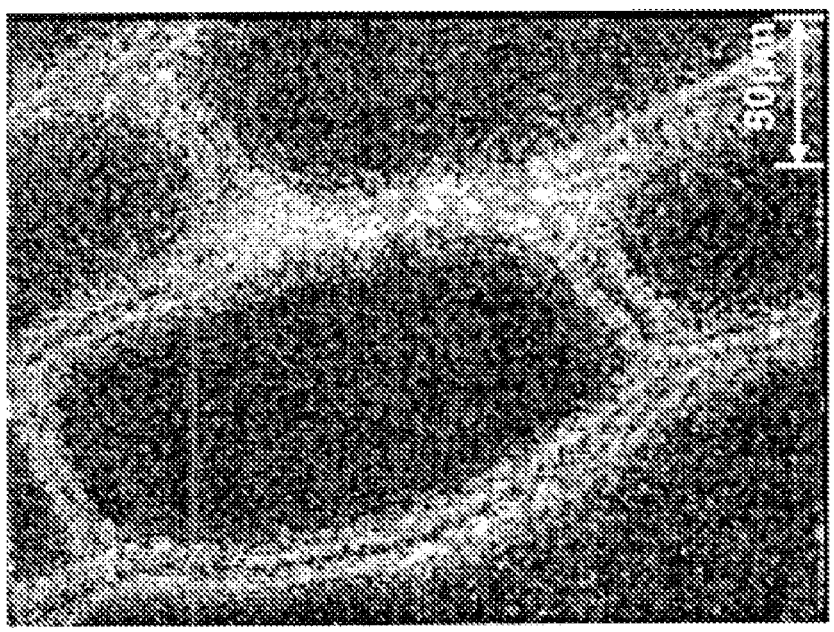
FIG. 7A is a 2PLSM image of an onion sample.

Another sample imaged was a ~50 μm thin slice of fresh onion skin that had been soaked in a Rhodamine 6G in water solution (10-3 molar) for six hours, as an example of 2PLSM applied to biological imaging. FIG. 7A shows a 2PLSM image of the onion sample, and FIG. 7B shows an image of the onion sample obtained by conventional white-light confocal microscopy. The structure of onion cell wall can be clearly identified. For this sample, the average power of the input optical wave 304 was about 22.3 mW, and no damage to the onion sample was observed through repeated scans.

Other embodiments are within the scope of the following claims.

What is claimed is:

1. A method for imaging a sample characterized by a limit on incident optical energy absorbed over a given time period, comprising:

providing at least one input optical wave that includes pulses that each have a full-width half-maximum time duration of more than 100 picoseconds and a pulse energy sufficiently large such that a sufficient number of consecutive pulses absorbed by the sample would exceed the limit;

directing the input optical wave to focus on a first portion of the sample;

detecting energy from an output optical wave generated from a nonlinear optical interaction in the first portion of the sample with the input optical wave; and generating a representation of the first portion of the sample based on the detected energy from the output optical wave.

2. The method of claim 1, wherein the input optical wave includes pulses that each have a full-width half-maximum time duration of more than 500 picoseconds.

3. The method of claim 2, wherein the input optical wave includes pulses that each have a full-width half-maximum time duration of more than 1 nanosecond.

4. The method of claim 3, wherein the input optical wave includes pulses that each have a full-width half-maximum time duration of more than 10 nanoseconds.

5. The method of claim 4, wherein the input optical wave includes pulses that each have a full-width half-maximum time duration of more than 100 nanoseconds.

6. The method of claim 1, further comprising temporarily preventing the input optical wave from reaching the sample.

7. The method of claim 6, wherein temporarily preventing the input optical wave from reaching the sample includes periodically preventing the input optical wave from reaching the sample.

8. The method of claim 6, wherein temporarily preventing the input optical wave from reaching the sample includes preventing the optical wave from reaching the sample before a number of consecutive pulses are absorbed by the sample would exceed the limit.

9. The method of claim 1, wherein the nonlinear optical interaction comprises multi-photon absorption.

10. The method of claim 9, wherein the nonlinear optical interaction comprises two-photon absorption.

11. The method of claim 10, wherein the output optical wave comprises a fluorescence emission from the sample.

12. The method of claim 11, wherein the fluorescence emission from the sample comprises emission from a fluorescent molecule in the sample.

13. The method of claim 1, wherein the nonlinear optical interaction comprises wave mixing.

14. The method of claim 13, wherein the nonlinear optical interaction comprises four-wave mixing.

15. The method of claim 14, wherein the nonlinear optical interaction comprises coherent anti-Stokes Raman scattering.

16. The method of claim 13, wherein providing at least one input optical wave, directing the input optical wave, and detecting energy from the output optical wave comprise:
providing at least two input optical waves that include pulses that each have a full-width half-maximum time duration of more than 100 picoseconds;
directing the input optical waves to focus on a first portion of the sample; and
detecting energy from an output optical wave generated from a wave mixing interaction in the first portion of the sample with each of the input optical waves.

17. The method of claim 16, wherein providing at least two input optical waves comprises providing signal and idler optical waves generated from parametric downconversion of a pump optical wave that includes pulses that each have a full-width half-maximum time duration of more than 100 picoseconds.

18. The method of claim 1, further comprising:
moving the input optical wave relative to the sample to focus on a second portion of the sample;
detecting energy from an output optical wave generated from a nonlinear optical interaction in the second portion of the sample with the input optical wave;
generating a representation of the second portion of the sample based on the detected energy from the output optical wave; and
generating an image of the sample that includes the representation of the first portion of the sample and the representation of the second portion of the sample.

19. A method for imaging a sample, comprising:
providing at least one input optical wave that includes pulses that are approximately uniformly spaced by a time delay;
directing the input optical wave to focus on a first portion of the sample;
detecting energy from an output optical wave generated from a nonlinear optical interaction in the first portion of the sample with the optical wave during a first time period that is about equal to or longer than the time delay;
temporarily preventing the input optical wave from reaching the sample during a second time period that is long enough for most of an amount of heat built up in the sample by the input optical wave during the first time period to be dissipated; and
generating a representation of the first portion of the sample based on the detected energy from the output optical wave.

20. The method of claim 19, wherein the first time period is short enough to prevent damage to the sample caused by the amount of heat built up in the sample by the input optical wave during the first time period.

21. The method of claim 19, wherein the first time period is shorter than 500 milliseconds.

22. The method of claim 21, wherein the first time period is shorter than 100 milliseconds.

23. The method of claim 22, wherein the first time period is shorter than 10 milliseconds.

24. The method of claim 23, wherein the first time period is shorter than 1 millisecond.

25. The method of claim 19, wherein the first time period is longer than twice the time delay.

26. The method of claim 19, wherein detecting the energy from the output optical wave and temporarily preventing the input optical wave from reaching the sample are repeated approximately periodically during multiple respective first and second time periods with the input optical wave directed to focus on different portions of the sample.

27. The method of claim 19, wherein detecting energy from the output optical wave during the first time period comprises processing detected energy during respective time windows that are shorter than the time delay and rejecting detected energy from the sample outside of the time windows.

28. The method of claim 27, wherein the time windows are synchronized to respective pulses in the input optical wave.

29. The method of claim 27, wherein rejecting detected energy from the sample outside of the time windows comprises preventing detection of energy from the sample outside of the time windows.

30. The method of claim 27, wherein rejecting detected energy from the sample outside of the time windows comprises preventing processing of portions of a stored signal that correspond to energy detected outside of the time windows.

31. The method of claim 19, further comprising moving the input optical wave relative to the sample to focus on a second portion of the sample.

32. The method of claim 31, wherein the input optical wave is moved relative to the sample during the second time period.

33. The method of claim 31, wherein moving the input optical wave relative to the sample comprises moving the input optical wave without moving the sample.

34. The method of claim 31, wherein moving the input optical wave relative to the sample comprises moving the sample without moving the input optical wave.

35. The method of claim 31, further comprising:
detecting energy from an output optical wave generated from a nonlinear optical interaction in the second portion of the sample with the input optical wave;
generating a representation of the second portion of the sample based on the detected energy from the output optical wave; and
generating an image of the sample that includes the representation of the first portion of the sample and the representation of the second portion of the sample.

36. The method of claim 19, wherein the input optical wave includes pulses that each have a full-width half-maximum time duration of more than 100 picoseconds.

37. The method of claim 36, wherein the input optical wave includes pulses that each have a full-width half-maximum time duration of more than 1 nanosecond.

38. The method of claim 19, wherein the time delay is between about 1 microsecond and about 1 millisecond.

39. The method of claim 38, wherein the time delay is between about 10 microseconds and about 100 microseconds.

40. The method of claim 19, wherein the nonlinear optical interaction comprises multi-photon absorption.

41. The method of claim 40, wherein the nonlinear optical interaction comprises two-photon absorption.

42. The method of claim 41, wherein the output optical wave comprises a fluorescence emission from the sample.

43. The method of claim 42, wherein the fluorescence emission from the sample comprises emission from a fluorescent molecule in the sample.

44. The method of claim 19, wherein the nonlinear optical interaction comprises wave mixing.

45. The method of claim 44, wherein the nonlinear optical interaction comprises four-wave mixing.

46. The method of claim 45, wherein the nonlinear optical interaction comprises coherent anti-Stokes Raman scattering.

47. The method of claim 44, wherein providing at least one input optical wave, directing the input optical wave, and detecting energy from the output optical wave comprise:
providing at least two input optical waves that include pulses;
directing the input optical waves to focus on a first portion of the sample; and
detecting energy from an output optical wave generated from a wave mixing interaction in the first portion of the sample with each of the input optical waves.

48. The method of claim 47, wherein providing at least two input optical waves comprises providing signal and idler optical waves generated from parametric downconversion of a pump optical wave that includes pulses.

49. A system for imaging a sample characterized by a limit on incident optical energy absorbed over a given time period, comprising:
a source of at least one input optical wave that includes pulses that each have a full-width half-maximum time duration of more than 100 picoseconds and a pulse energy sufficiently large such that a sufficient number of consecutive pulses absorbed by the sample would exceed the limit;
a microscope configured to direct the input optical wave to focus on a first portion of the sample; and
a detection sub-system configured to
detect energy from an output optical wave generated from a nonlinear optical interaction in the first portion of the sample with the input optical wave, and
generate a representation of the first portion of the sample based on the detected energy from the output optical wave.

50. The system of claim 49, wherein the source is configured to temporarily prevent the input optical wave from reaching the sample.

51. The system of claim 50, wherein temporarily preventing the input optical wave from reaching the sample includes periodically preventing the input optical wave from reaching the sample.

52. The system of claim 50, wherein temporarily preventing the input optical wave from reaching the sample includes preventing the optical wave from reaching the sample before a number of consecutive pulses are absorbed by the sample would exceed the limit.

53. The system of claim 49, further comprising excitation optics between the source and the microscope configured to periodically prevent the input optical wave from reaching the sample.

54. The system of claim 49, wherein the detection sub-system is configured to process energy that has been detected within time windows corresponding to the pulses.

55. The system of claim 54, wherein the detection sub-system is configured to prevent detection of energy outside of the time windows.

56. The system of claim 54, wherein the detection sub-system is configured to remove portions of a signal corresponding to energy detected outside of the time windows.

* * * * *